United States Patent
Vironda

[11] 3,981,298
[45] Sept. 21, 1976

[54] METHOD OF TREATING INGROWN NAIL

[76] Inventor: Philip G. Vironda, 71 S. LaVista Blvd., Battle Creek, Mich. 49015

[22] Filed: July 23, 1973

[21] Appl. No.: 381,603

[52] U.S. Cl. ............................................. 128/81 R
[51] Int. Cl.² ............................................ A61F 5/00
[58] Field of Search............ 128/81 A, 81 R; 132/73, 132/88.5; 424/61, 81

[56] References Cited
UNITED STATES PATENTS

| | | | |
|---|---|---|---|
| 2,342,530 | 2/1944 | Coates | 128/81 A |
| 2,505,086 | 4/1950 | Andrews | 128/81 A |
| 3,257,280 | 6/1966 | Richter | 424/61 |
| 3,382,151 | 5/1968 | Knudsen | 424/61 |
| 3,483,289 | 12/1969 | Michaelson et al. | 424/61 |
| 3,510,554 | 5/1970 | Balsiger | 424/61 |
| 3,574,822 | 4/1971 | Shepherd et al. | 424/61 |
| 3,750,684 | 8/1973 | Russell | 132/88.5 |

*Primary Examiner*—John D. Yasko
*Attorney, Agent, or Firm*—Samuel Kurlandsky

[57] ABSTRACT

A method of treating a toenail or fingernail for correcting an ingrown condition which comprises applying a material in flowing or liquid form across the nail at the base or proximal portion in a limited area having a normal radius of curvature, causing the material to harden and to become adhered to the nail and to serve as a form-retaining support, permitting the support to remain adhered to the nail as the nail grows over a period of time until the coated and supported portion extends beyond the end of the toe, and removing the portion of the nail having the coated material thereon, the nail remaining being partially or totally cured of the ingrown condition.

10 Claims, 10 Drawing Figures

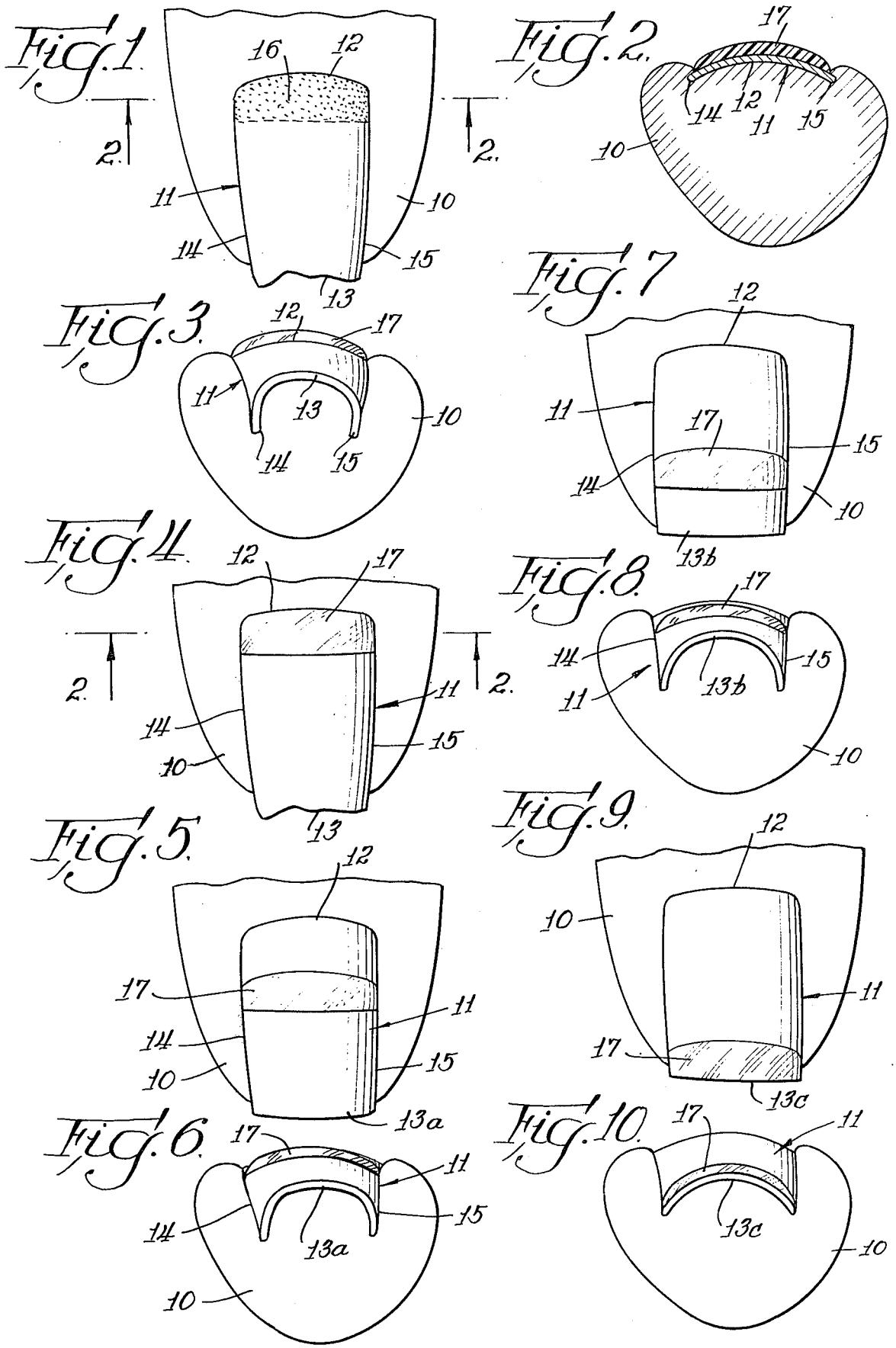

METHOD OF TREATING INGROWN NAIL

BACKGROUND OF THE INVENTION

The present invention relates to a method of treatment, and more particularly refers to a method for correcting the condition known as ingrown toenail or ingrown fingernail.

The normal nail of a toe or finger has a large radius of curvature at its base or proximal portion, with the radius of curvature remaining large throughout the length and even at the end or distal portion of the nail. However, certain conditions may result in which the edge or edges of the nail become involuted particularly at or near the distal portion of the nail, and the radius of curvature becomes increasingly smaller. As a result, the inturned or involuted edge or edges of the nail in that region deform or penetrate the flesh of the toe, causing severe pain and discomforture, giving rise to the conditions known as ingrown toenail or ingrown fingernail.

Numerous devices have been tried in the prior art to correct the ingrown nail condition. Among such devices are metal bands, metal hooks, plastic hooks, and even preformed plastic sheets which are adhesively affixed to the nail. However, many of the devices are painful to use, cause extended discomforture, and are generally ineffective. Additionally, such devices are generally quite expensive and require precise fitting by an expert.

SUMMARY OF THE INVENTION

It is accordingly an object of the invention to provide a method of treating toenails or fingernails to correct the conditions known as ingrown toenail or ingrown fingernail, which method is more effective than prior art means.

It is a further object to provide a method of the type described which does not require expensive mechanical devices.

It is still another object to provide such a method which does not necessarily require the services of a physician or podiatrist, but which may be safely and effectively carried out by the patient or subject himself.

It is still an additional object to provide a method of the type described which is painless and which does not leave the toenail or fingernail in an abnormal condition.

Still other objects will readily present themselves to one skilled in the art upon reference to the following specification, the drawing, and the claims.

According to the invention, a flowing or liquid material is applied as a band across substantially the entire width of the base or proximal portion of the nail which has a normal radius of curvature and is not deformed. The material is caused to harden and to adhere to the nail thereby providing a substantially rigid band or supporting structure adhered to the nail. The nail is then permitted to grow. As the nail grows out, the supporting band follows the growth of the nail and forces that area of the nail to which it is adhered to retain its original long radius of curvature as it grows forwardly. The nail is permitted to grow until the coating reaches the forward or distal portion of the toe. Since the portion to which the material is adhered has been forced to maintain substantially its original long radius of curvature, the original ingrown condition has been corrected, or at least alleviated to a marked degree. The coating material may at this point be removed with a solvent or heat, or permitted to grow sufficiently beyond the end of the toe so that the coated nail portion may be cut off. The unsupported end or distal portion of the nail now has a normal radius of curvature and the previous ingrown condition has been corrected or at least greatly improved.

BRIEF DESCRIPTION OF THE DRAWING

In the drawing,

FIG. 1 is a top view showing the extremity of a toe having a toenail in an ingrown condition.

FIG. 2 is a cross-sectional view taken at the line 2—2 of FIG. 4, looking in the direction of the arrows, showing a coating according to the invention applied to the base portion of the nail.

FIG. 3 is an end view of the toe showing the rear portion of the nail coating, and showing the ingrown condition of the forward or distal portion of the toenail.

FIG. 4 is a top view of the toe and coated nail shown in FIGS. 2 and 3.

FIG. 5 is a top view of the toe and coated nail showing a somewhat advanced stage of growth of the nail.

FIG. 6 is a front end view of the toe and nail shown in FIG. 5.

FIG. 7 is a top view of the toe and nail in a further advanced condition of growth.

FIG. 8 is a front end view of the toe and nail shown in FIG. 7.

FIG. 9 is a top view of the toe and nail showing the coating area advanced to the end of the nail and at the end of the toe, and FIG. 10 is a front end view of the toe and nail shown in FIG. 9.

DESCRIPTION OF THE PREFERRED EMBODIMENT

Referring to FIG. 1, the end of a toe 10 is shown having a toenail 11 thereon. The exposed portion of the toenail 11 has a base or proximal end 12 and a forward or distal end 13. The proximal end 12 has a normal large radius of curvature, as shown in FIG. 2, whereas the distal end 13 has a considerably smaller radius of curvature caused by involution of the edges 14 and 15 of the nail which have become squeezed into or embedded in the flesh of the toe, a condition commonly known as ingrown toenail.

In preparation for applying the adhesive material of the invention to the base of a toenail, an area 16 of the toenail may be roughened by means of sandpaper or an emery board in order to provide for better adhesion. The liquid or flowing adhesive supporting material is then applied in the form of a strip 17 across substantially the entire width of the nail, as shown in FIGS. 2 and 3. The preferred material is methylmethacrylate, also known by the trade names "Plexiglas" and "Lucite." A particularly desirable material is a mixture of methyl-methacrylate polymer and monomer. Other materials may be used such as epoxy resins, polystyrene, polyvinyl chloride, polyurethane, and other resinous materials. Additionally, waxy materials may be utilized which become stiff upon hardening. The primary desirable attributes of a material are that the material adhere well to the surface of a nail, and that upon hardening it becomes substantially rigid so that it retains its original hardened shape even when subjected to the forces which tend to cause the nail to become involute as it grows forward. The material may be one that hardens upon standing at room temperature such as the polymethylmethacrylate mixture described above, or epoxy resins utilizing a catalyst for hardening. Additionally, the material may be one which is heated to render it soft or liquid and which hardens again upon returning to room temperature. However, the softening or melting point of the material must not be so high that it might cause pain or injury when applied in soft form to the surface of the nail. Additionally, a reinforcing material such as fiberglass fabric may be embedded in the softened material.

The relative proportion of the nail which is covered by the supporting material is not critical. Generally the material should be applied at the base or proximal end of the toe and substantially across the entire width. The width is not critical, although a width of ⅛ inch to 3/16 inch is satisfactory. The width may be made greater, but it is desirable that the area covered should not extend over a portion of the nail which is in the ingrown condition or having a low radius of curvature. The thickness also is not critical although a thickness of about 1/16 inch is desirable. If the thickness is too small, particularly with softer materials, the supporting material will not be sufficiently rigid to retain the original shape having a long radius of curvature, but will be forced to bend with the ingrown portion of the nail. If the material is applied too thick, it may prove to be uncomfortable during the period of treatment.

Referring to FIGS. 5 and 6, the condition of the toenail is shown after a growth period of 2 months after application of the band of supporting material 17. As shown in FIGS. 5 and 6, the band 17 has moved forwardly and has progressed to a point about one-third of the length of the nail from the base. As shown in FIG. 6, the radius of curvature of the forward portion 13a of the nail has increased substantially, showing a marked improvement.

Referring to FIGS. 7 and 8, the supporting band 17 has now after about 4 months moved about two-thirds along the length of the nail from the base. As shown in FIG. 8, the radius of curvature of the end 13b of the nail has increased still further, but is still not quite normal.

FIGS. 9 and 10 illustrate the toe and nail wherein the supporting band 17 has progressed until it extends beyond the supporting pulp of the toe. As seen in FIG. 10, the radius of curvature of the end 13c of the toenail has now increased until the curvature is normal, the ingrown toenail condition now having been completely alleviated. The overhanging portion of the toenail together with the supporting band may now be cut off and the nail is now in normal condition. Alternatively, the material may be removed at this point or even earlier by means of a solvent when a soluble material is utilized, or by heat when a fusible material is utilized. In the case of subsequent reoccurence of the ingrown condition, or if a complete cure is not obtained with a single treatment, the treatment described may be repeated.

EXAMPLE I

The base portion at the cuticle of a patient's toenail in ingrown condition was roughened with an emery board. A mixture of polymethylmethacrylate polymer in powder form and a monomer of polymethylmethacrylate in liquid form and containing a catalyst, such as commonly used by dentists in making dental appliances such as dentures and partials, was mixed together and applied as a band about 3/16 inch wide and about 1/16 inch thick across the entire width of the toenail. The resinous mixture was then permitted to harden at room temperature, and upon hardening it formed a substantially rigid supporting band. The band was permitted to remain on the toe for a period of 6 months, at the end of which time the banded portion of the nail was completely free of the toe. The nail was cut to remove the band, leaving a free edge of substantially normal radius of curvature with the ingrown condition substantially eliminated.

The correcting band of hardened material may be left in place and trimmed along with the nail as natural growth of the nail demands, until such time as the ingrowing tendency is cured and the nail has grown sufficiently to overlap the toe. At this time the nail may be cut with the remaining portion of the plastic band. Alternatively the band may be left in place until natural growth has completely replaced the coated portion, and the nail supporting the entire band cut off. The coating material may be either natural or may be colored in flesh tone. Alternatively the band may be removed by solvent means or heat before it has grown completely beyond the toe. The invention may also be used for treating ingrown fingernails.

The method of the present invention has a number of features which render it superior to prior art methods and devices. First, no expensive devices are required which must be precisely manufactured and fitted. The use of the method results in no pain or discomforture to the patient or subject during the entire period of treatment. The material for forming the supporting band is relatively inexpensive and readily available. The application of the material and the formation of the band does not require a skilled operator and may be performed even by the patient or subject himself. The use of the method results in substantial elimination of the ingrown condition or substantial improvement thereof. If the condition is not completely eliminated after the first application, the treatment may be repeated with no adverse results and with generally substantial improvement or complete elimination of the condition.

It is to be understood that the invention is not to be limited to the exact details of operation or structures shown and described, as obvious modifications and equivalents will be apparent to one skilled in the art.

I claim:

1. A method for treating an ingrown nail condition which comprises applying a coating consisting essentially of a hardenable substantially liquid material having adhesive properties with respect to the surface of the nail over a rearwardly disposed limited area substantially across the entire width of the nail and at an area having a substantially normal radius of curvature, permitting said material to harden and to become affixed to the surface of the nail to form a support, and permitting the hardened material to remain on said nail until it has progressed forwardly to a position at the forward end of said nail and has substantially increased the radius of curvature at the forward end of the nail, and removing said hardened material, the thickness of said coating being sufficient to retain substantially the curvature of the coated portion of said nail as it grows to the end of the toe and is eventually removed.

2. A method according to claim 1, wherein said substantially liquid material is a plastic liquid hardenable at room temperature.

3. A method according to claim 2, wherein said plastic liquid comprises a mixture of polymeric and monomeric methylmethacrylate and a catalyst therefor.

4. A method according to claim 2, wherein said plastic liquid is an epoxy resin containing a catalyst and hardenable at room temperature.

5. A method according to claim 1, wherein said material is applied at the base of the nail in a strip extending substantially across the entire width of the nail.

6. A method according to claim 5, wherein said strip is about 1/16 inch thick and about 1/8 to 3/16 inch wide.

7. A method according to claim 1, wherein said nail is a toenail.

8. A method according to claim 1, wherein said hardened material is subsequently removed from said nail by means of a solvent.

9. A method according to claim 1, wherein said hardened material is subsequently removed from said nail by application of heat.

10. A method according to claim 7, wherein said hardened material is subsequently removed from said nail by cutting off the coated portion of said nail when said coating is on a free portion thereof extending beyond the end of the toe supporting said nail.

* * * * *